US010255828B2

(12) United States Patent
Snyder

(10) Patent No.: US 10,255,828 B2
(45) Date of Patent: Apr. 9, 2019

(54) APPARATUS FOR RELEASABLY AND ADJUSTABLY MOUNTING A TUBULAR DEVICE TO AN OBJECT

(71) Applicant: Stephen J. Snyder, Van Nuys, CA (US)

(72) Inventor: Stephen J. Snyder, Van Nuys, CA (US)

( * ) Notice: Subject to any disclaimer, the term of this patent is extended or adjusted under 35 U.S.C. 154(b) by 0 days.

(21) Appl. No.: 15/806,435

(22) Filed: Nov. 8, 2017

(65) Prior Publication Data

US 2018/0130380 A1 May 10, 2018

Related U.S. Application Data

(60) Provisional application No. 62/419,766, filed on Nov. 9, 2016.

(51) Int. Cl.
G09B 23/28 (2006.01)
G09B 23/30 (2006.01)
A61B 1/317 (2006.01)

(52) U.S. Cl.
CPC ............ G09B 23/285 (2013.01); A61B 1/317 (2013.01); G09B 23/30 (2013.01)

(58) Field of Classification Search
CPC ...... G09B 23/28; G09B 23/285; G09B 23/30; G09B 23/306
USPC .......................... 434/262, 267, 272, 274, 275
See application file for complete search history.

(56) References Cited

U.S. PATENT DOCUMENTS

| 6,470,302 | B1* | 10/2002 | Cunningham | G09B 23/28 128/897 |
| 6,902,405 | B2* | 6/2005 | Irion | G05G 9/047 434/262 |
| 7,594,815 | B2* | 9/2009 | Toly | G09B 23/285 434/262 |
| 8,007,281 | B2* | 8/2011 | Toly | A61B 90/36 434/262 |
| 8,157,567 | B2* | 4/2012 | Chen | G09B 23/285 434/262 |
| 8,328,560 | B2* | 12/2012 | Niblock | A61B 34/76 434/262 |
| 9,827,050 | B2* | 11/2017 | Johansson | G09B 23/285 |
| 2014/0303631 | A1 | 10/2014 | Thornberry | |
| 2016/0117956 | A1* | 4/2016 | Larsson | G09B 23/285 434/262 |

* cited by examiner

*Primary Examiner* — Kurt Fernstrom
(74) *Attorney, Agent, or Firm* — Pandiscio & Pandiscio

(57) ABSTRACT

Apparatus for releasably and adjustably mounting a tubular device to an object, the apparatus comprising: a base comprising a central opening passing therethrough, the base being magnetized so as to provide a magnetic field at the central opening of the base; a generally spherical ball sized to be received in the central opening of the base but sized so as to not pass through the central opening, the generally spherical ball comprising a central bore passing therethrough; wherein the ball comprises a ferrous material which is attracted to the magnetic field at the central opening of the base, and further wherein the magnetic field at the central opening of the base is sufficiently strong so as to retain the ball in the central opening of the base; and wherein the central bore of the generally spherical ball is configured to slidably receive a tubular device therein, and further wherein the base is configured to be mounted to an object.

18 Claims, 17 Drawing Sheets

APPARATUS FOR RELEASABLY AND ADJUSTABLY MOUNTING A TUBULAR DEVICE TO AN OBJECT

REFERENCE TO PENDING PRIOR PATENT APPLICATION

This patent application claims benefit of prior U.S. Provisional Patent Application Ser. No. 62/419,766, filed Nov. 9, 2016 by Stephen J. Snyder for MagneFAST™ Holder, which patent application is hereby incorporated herein by reference.

FIELD OF THE INVENTION

This invention relates to apparatus for mounting a tubular device to an object, and more particularly to a novel mount for releasably and adjustably mounting a scope (e.g., an endoscope, an arthroscope, etc.) or any other tubular device to an endoscopic training apparatus.

BACKGROUND OF THE INVENTION

Endoscopic (or arthroscopic, or laparoscopic, etc.) surgery is minimally-invasive, meaning that it is surgery which is performed though small incisions made in the patient's skin. In an endoscopic surgical procedure, the surgeon typically inserts a scope (e.g., an endoscope, an arthroscope, etc.), which is connected to a digital video camera, into an incision made in the skin of the patient in order to remotely view the surgical site. The digital video camera projects an image of the inside of the body cavity onto a video screen. The surgeon then inserts surgical tools into the same body cavity (e.g., through the same incision, through a second incision, through a cannula, etc.) and uses the surgical tools to perform the surgical procedure. Since the surgeon is using his/her hands for the surgery, he/she requires an assistant to hold the camera (i.e., the scope to which the digital video camera is attached) in order to visualize the surgical site.

Surgeons often learn (or practice) endoscopic techniques by practicing on a "simulator" or other training device replicating human anatomy. For the purposes of describing the present invention, such training devices will hereinafter generally be referred to as an "endoscopic training apparatus".

Looking now at FIG. 1, there is shown an exemplary endoscopic training apparatus 5. Endoscopic training apparatus 5 generally comprises a baseplate 10 which is covered by a dome 15. Dome 15 may be opaque or translucent/transparent (although for training purposes, an opaque dome is generally preferred) and typically comprises a plurality of openings 20 which pass through the dome and are disposed across the surface of the dome. Openings 20 are intended to simulate the incisions through which the surgeon performs an endoscopic procedure.

Looking next at FIG. 2, baseplate 10 generally comprises a central seat 25 for mounting a model 30 (FIG. 3), e.g., a humeral model, a scapular model, etc., which the surgeon uses to simulate an endoscopic surgical procedure.

Looking next at FIGS. 3 and 4, in use, a scope 35 (e.g., an endoscope, an arthroscope, etc.) that is connected to a digital video camera is inserted into a first opening 20 formed in dome 15 and held in place by an assistant. The surgeon can then practice performing an endoscopic surgical procedure on model 30 by inserting appropriate surgical instruments through a second opening 20 formed in dome 15 (while simultaneously viewing the procedure as it is performed within the dome on a video screen showing the output from the digital video camera). Thus, endoscopic training apparatus 5 generally requires two people (i.e., the surgeon practicing the endoscopic surgical procedure and an assistant who holds scope 35 in place during the simulated procedure) in order for the surgeon to practice an endoscopic surgical procedure (or learn a new endoscopic surgical procedure). As in an actual endoscopic surgical procedure, an assistant holds (and constantly adjusts) scope 35 (i.e., the camera) while the surgeon learns and practices the surgical repair technique.

However, it has been recognized that it would be desirable for the surgeon to be able to practice an endoscopic procedure without requiring an assistant to be present in order to hold scope 35 in position.

Thus there is a need for a new and improved mount for releasably and adjustably holding a scope in place on an endoscopic training apparatus which eliminates the need for a second person when a surgeon (or student) trains using an endoscopic training apparatus.

SUMMARY OF THE INVENTION

The present invention comprises the provision and use of a new and improved mount for releasably and adjustably holding a scope in place on an endoscopic training apparatus which eliminates the need for a second person when a surgeon (or student) trains using an endoscopic training apparatus.

In one preferred form of the present invention, there is provided apparatus for releasably and adjustably mounting a tubular device to an object, said apparatus comprising:

a base comprising a central opening passing therethrough, said base being magnetized so as to provide a magnetic field at said central opening of said base;

a generally spherical ball sized to be received in said central opening of said base but sized so as to not pass through said central opening, said generally spherical ball comprising a central bore passing therethrough;

wherein said ball comprises a ferrous material which is attracted to the magnetic field at said central opening of said base, and further wherein said magnetic field at said central opening of said base is sufficiently strong so as to retain said ball in said central opening of said base; and wherein said central bore of said generally spherical ball is configured to slidably receive a tubular device therein, and further wherein said base is configured to be mounted to an object.

In another preferred form of the present invention, there is provided a method for releasably and adjustably mounting a scope to an endoscopic training apparatus, said method comprising:

providing apparatus comprising:

a base comprising a central opening passing therethrough, said base being magnetized so as to provide a magnetic field at said central opening of said base;

a generally spherical ball sized to be received in said central opening of said base but sized so as to not pass through said central opening, said generally spherical ball comprising a central bore passing therethrough;

wherein said ball comprises a ferrous material which is attracted to the magnetic field at said central opening of said base, and further wherein said magnetic field at said central opening of said base is sufficiently strong so as to retain said ball in said central opening of said base; and wherein said central bore of said generally spherical ball is configured to slidably receive a scope therein, and further wherein said base is configured to be mounted to an endoscopic training apparatus;

mounting said base to an endoscopic training apparatus such that said central opening of said base and said central bore of said generally spherical ball are aligned with an opening in the endoscopic training apparatus; and disposing a scope in said central bore of said generally spherical ball such that the scope is releasably and adjustably retained in said central bore of said generally spherical ball.

In another preferred form of the present invention, there is provided apparatus for releasably and adjustably mounting an anatomical model to an object, said apparatus comprising:

a base;

a body slidably mounted to said base by a pair of diametrically-opposed set screws; and a post pivotally mounted to the base, said post being configured to be selectively pivoted by rotation of a lever.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention comprises the provision and use of a new and improved mount for releasably and adjustably holding a scope in place on an endoscopic training apparatus which eliminates the need for a second person when a surgeon (or student) trains using an endoscopic training apparatus.

Figure 1:
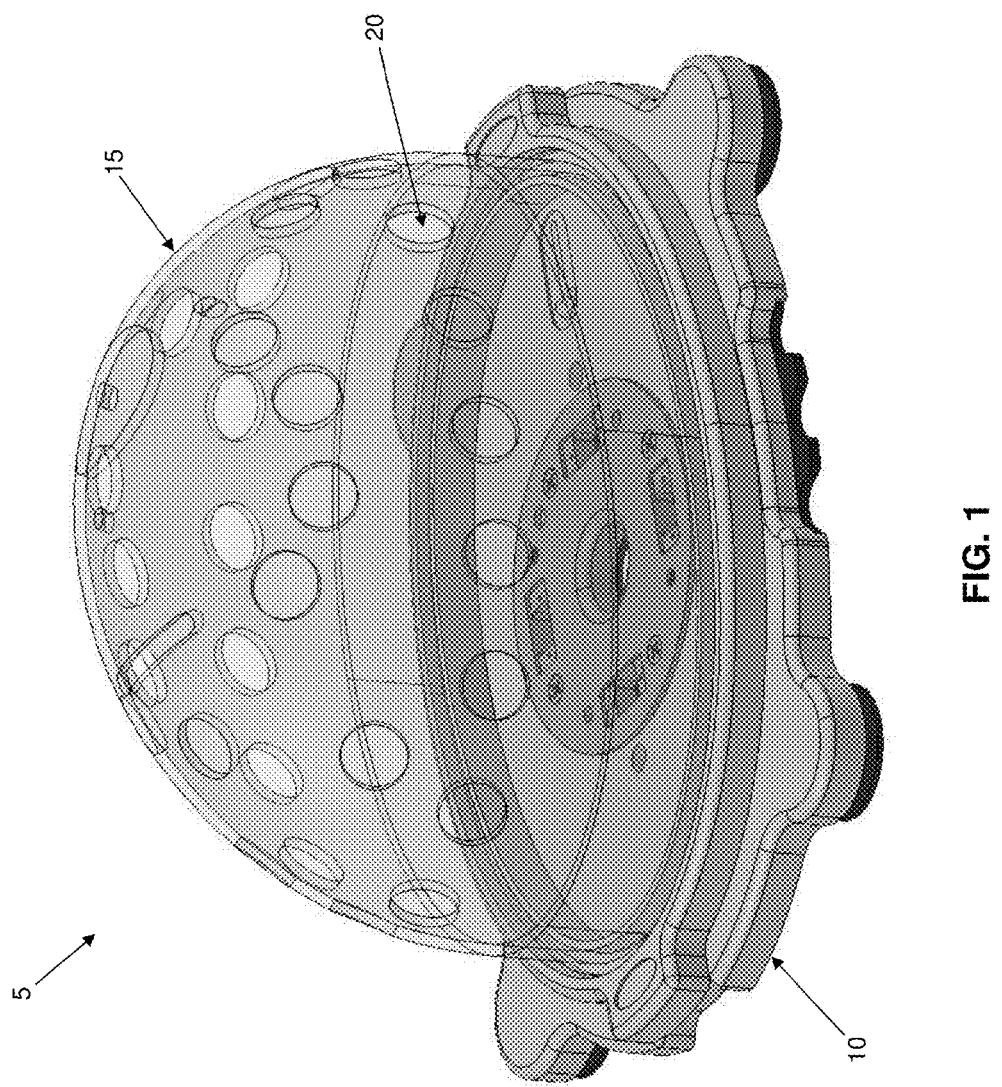
FIGS. 1-4 are schematic views showing an exemplary endoscopic training apparatus.
Figure 2:
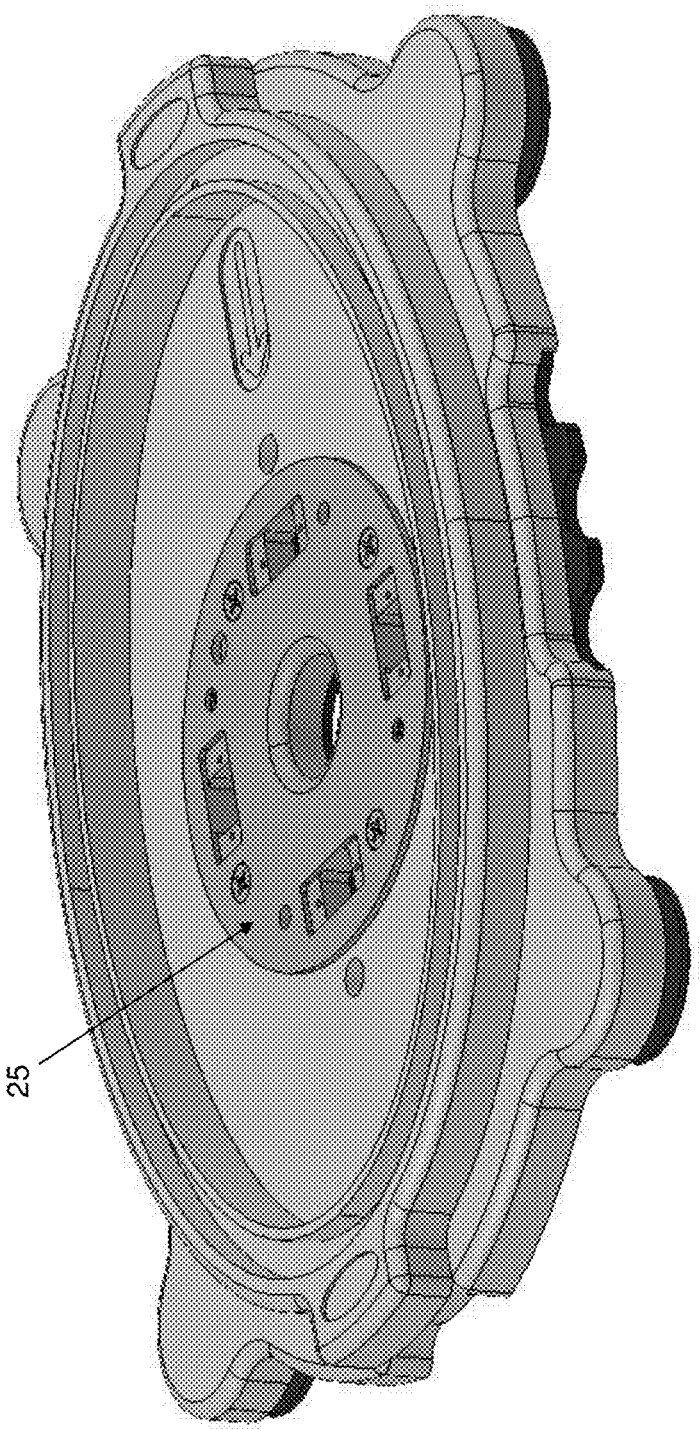
Figure 3:
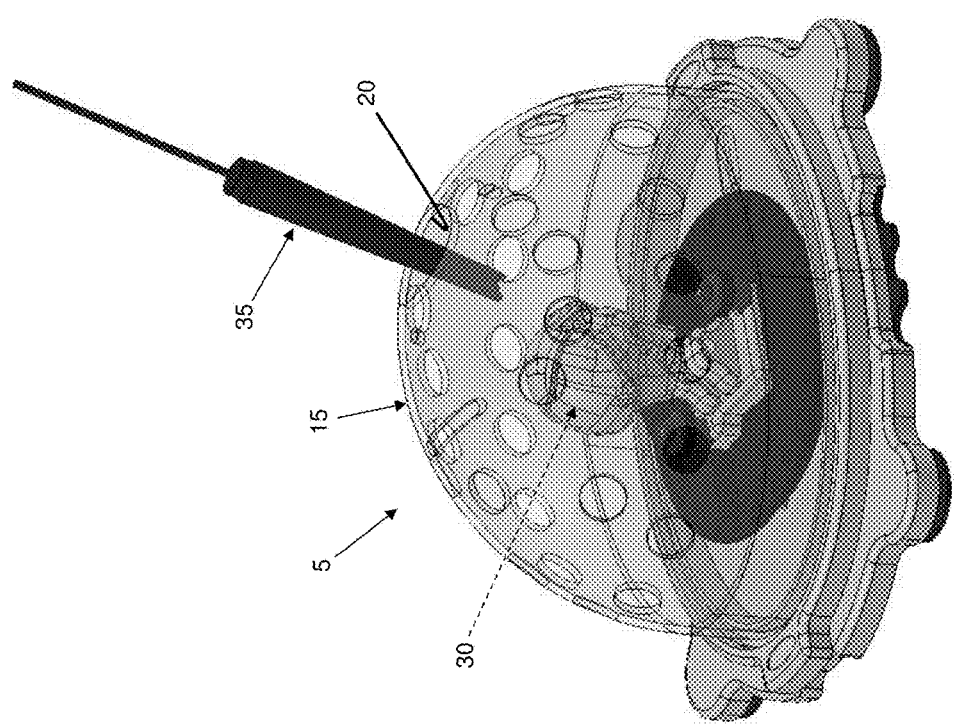
Figure 4:
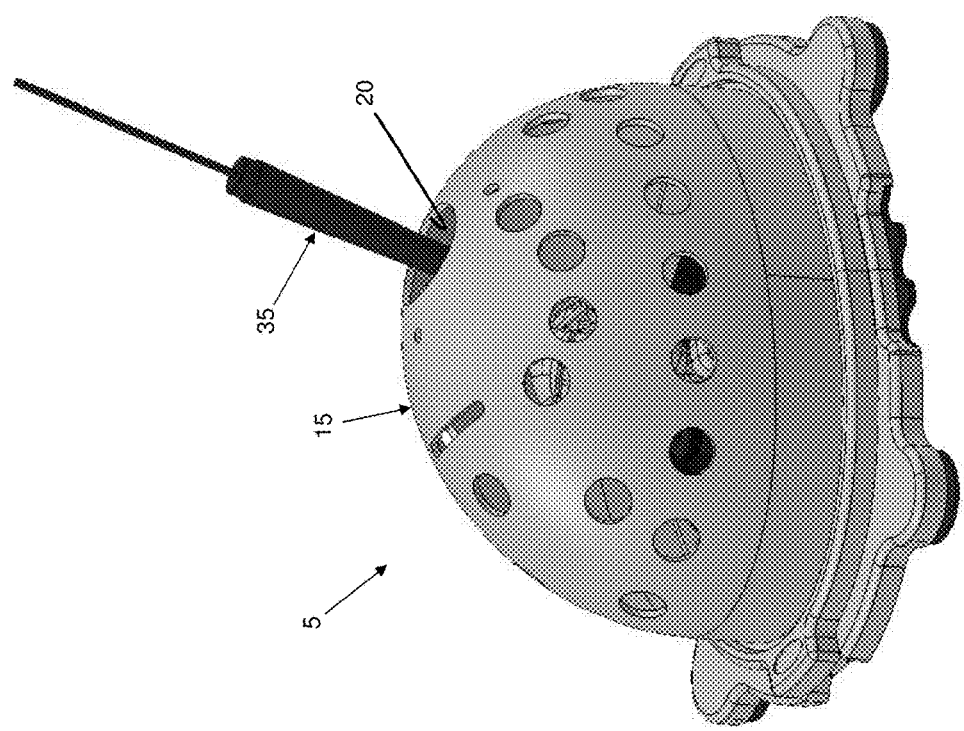
Figure 5:
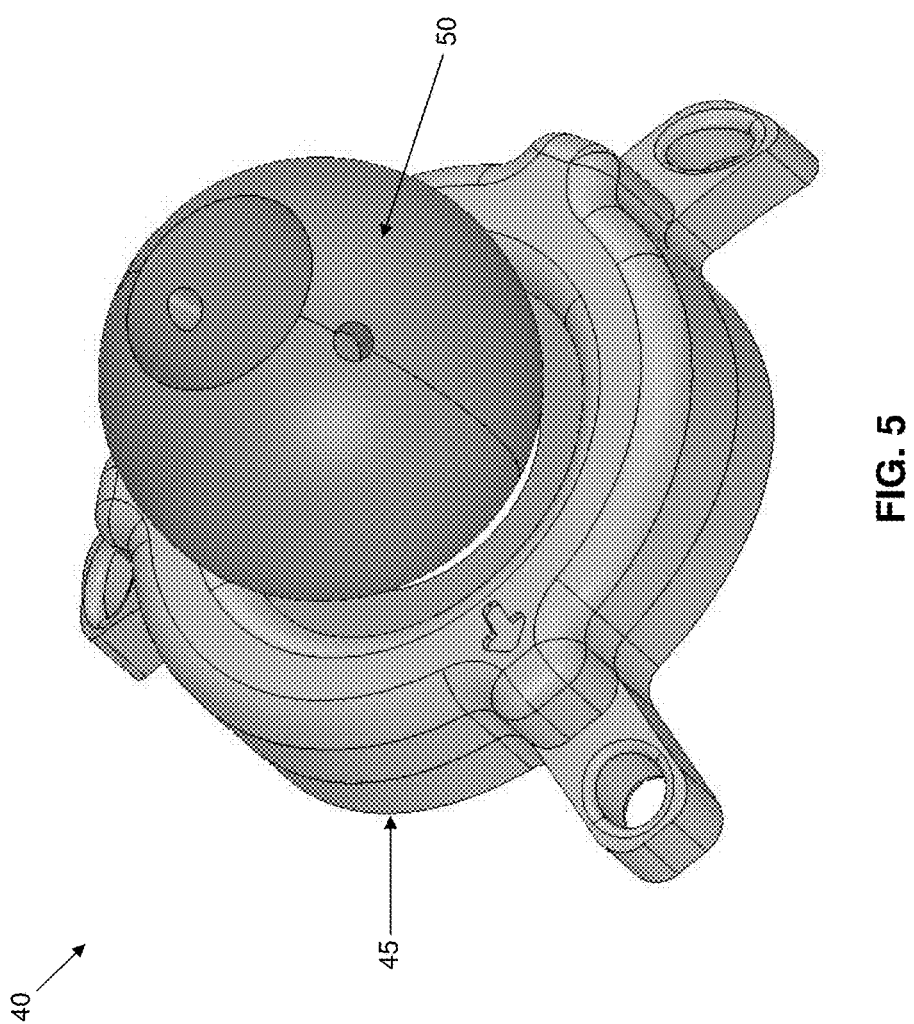
FIGS. 5-7 are schematic views showing a novel mount for mounting a scope to an endoscopic training apparatus.
Figure 6:
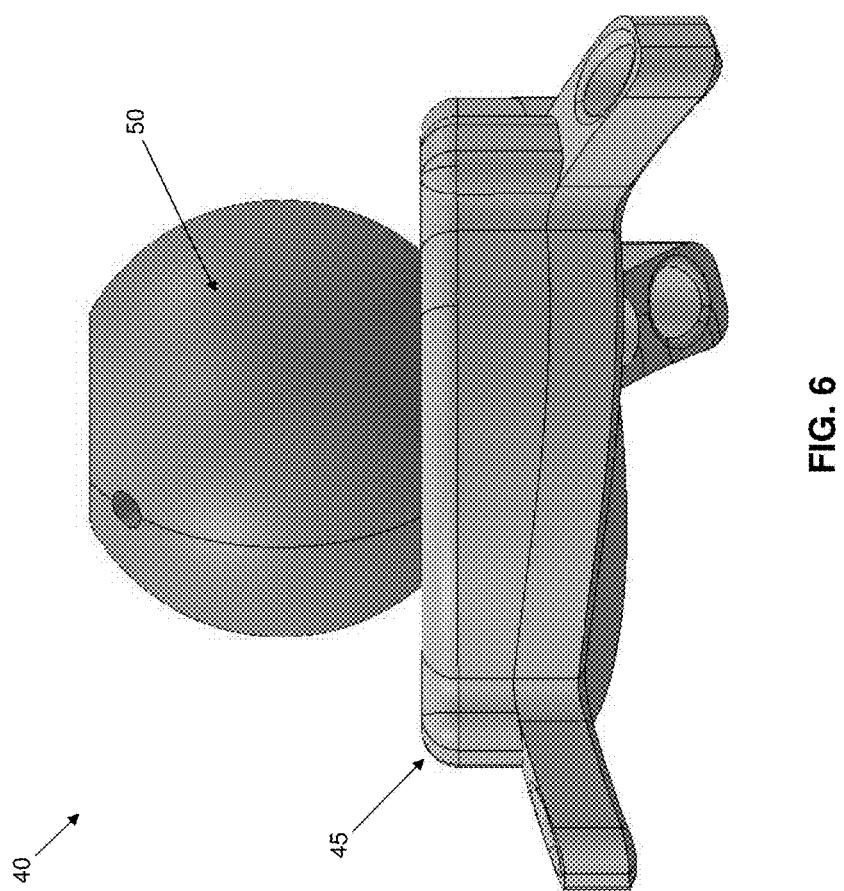
Figure 7:
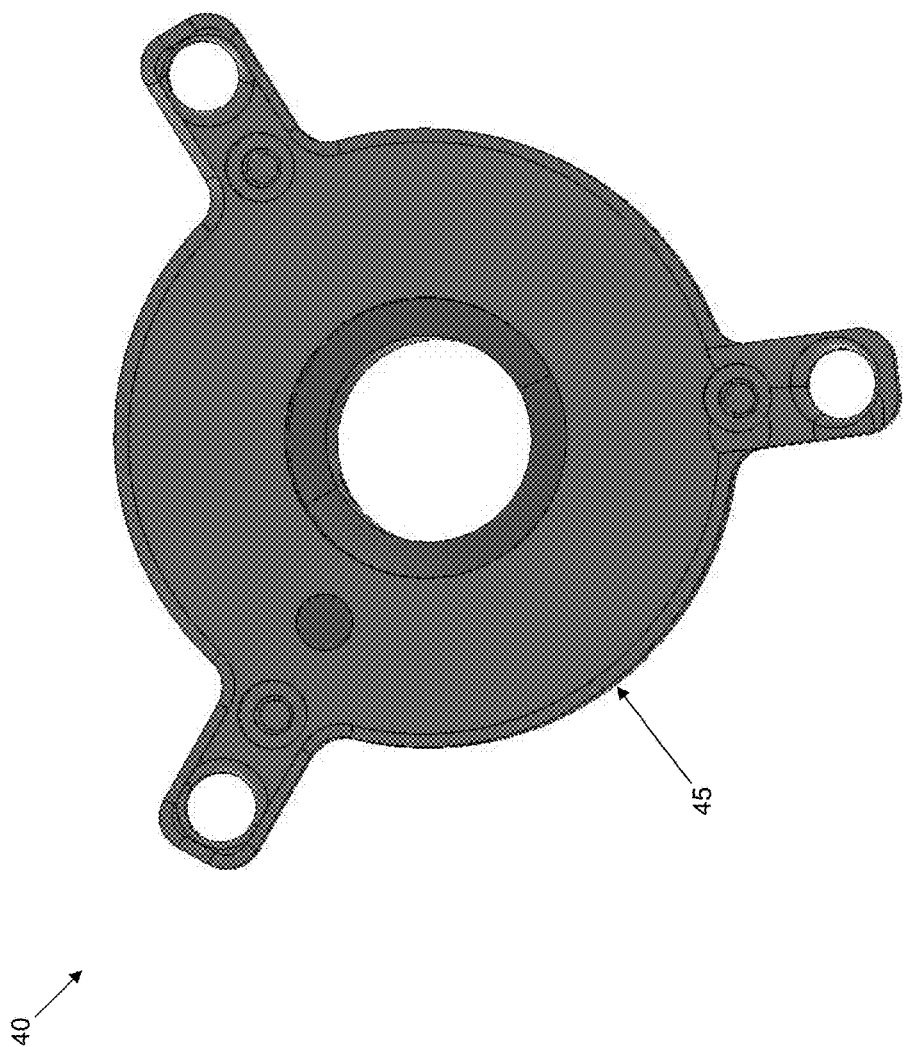

More particularly, and looking now at FIGS. 5-7, there is shown a novel mount 40 formed in accordance with the present invention. Mount 40 generally comprises a base 45 and a metallic (e.g., steel) ball 50 which is sized to be received within, and retained by, base 45, as will hereinafter be discussed.

Figure 8:
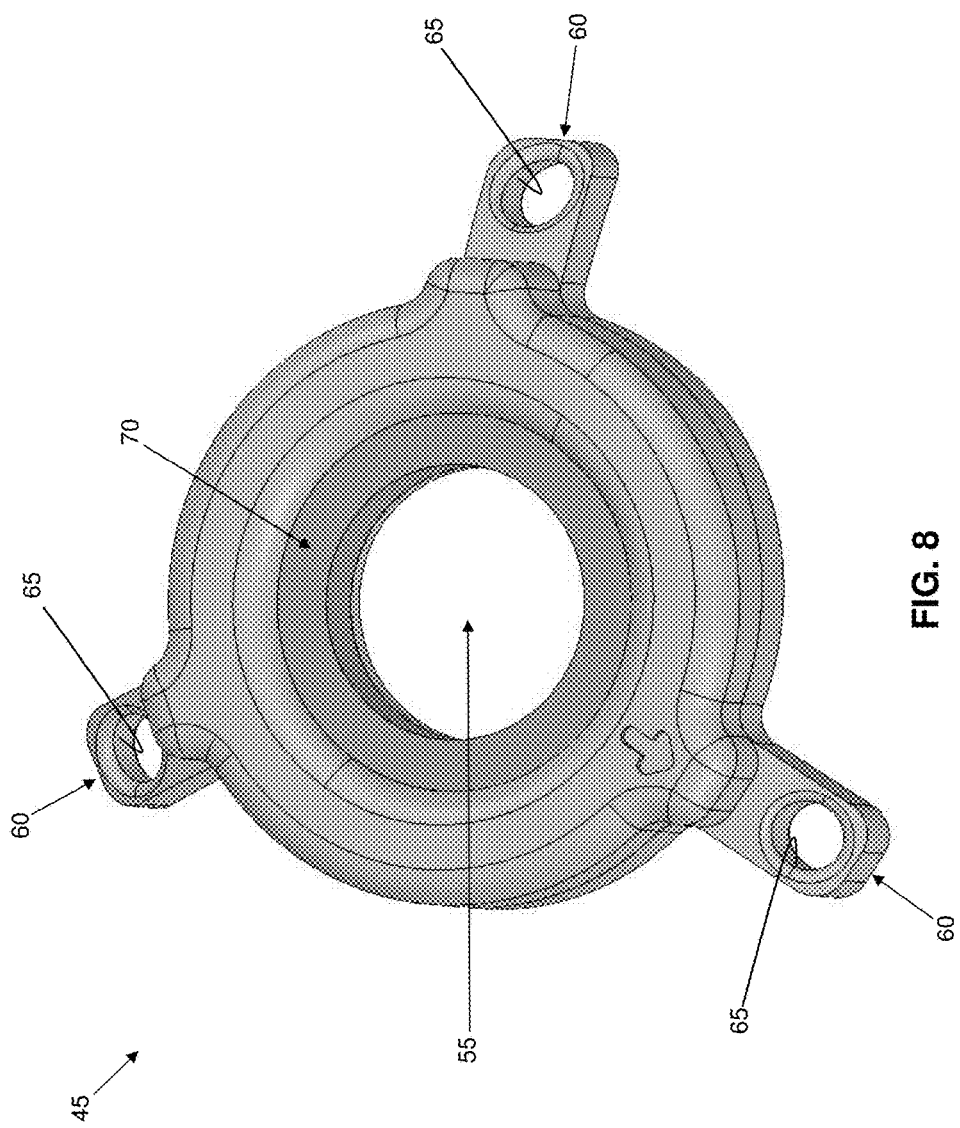
FIGS. 8-10 are schematic views showing further aspects of the novel mount shown in FIGS. 5-7.
Figure 15:
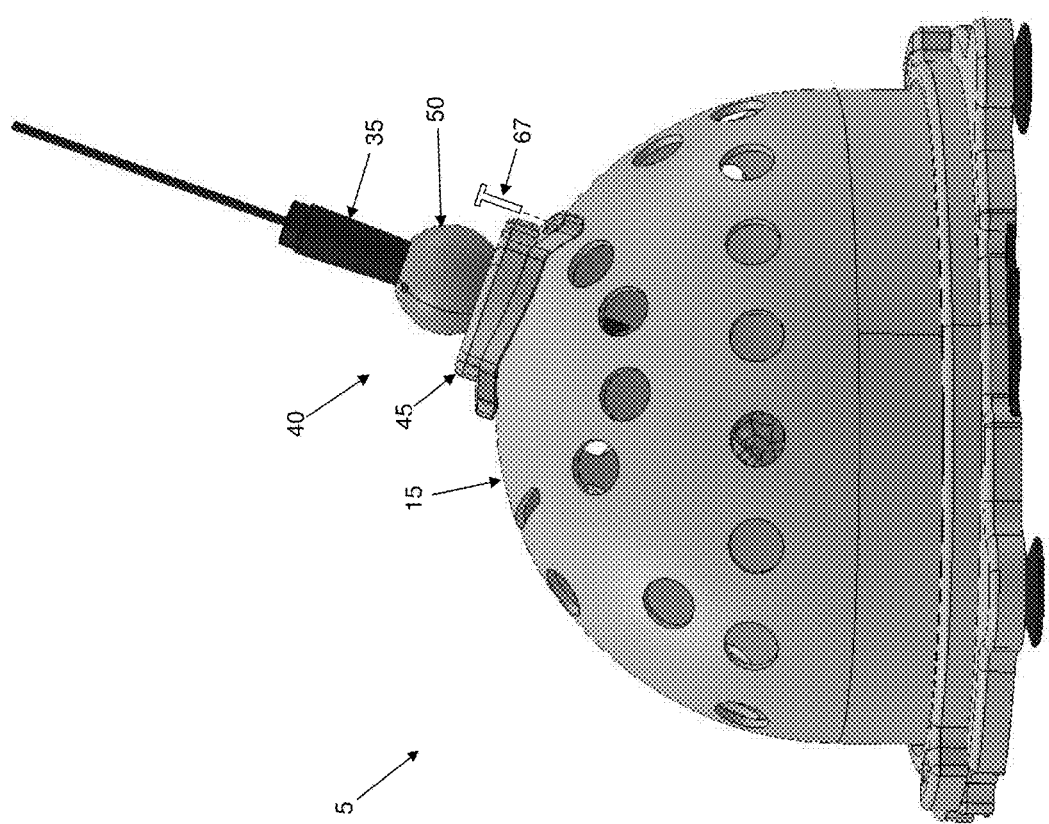
FIGS. 15 and 16 are schematic views showing the novel mount of FIGS. 5-7 mounted to an endoscopic training apparatus and supporting a scope.
Figure 16:
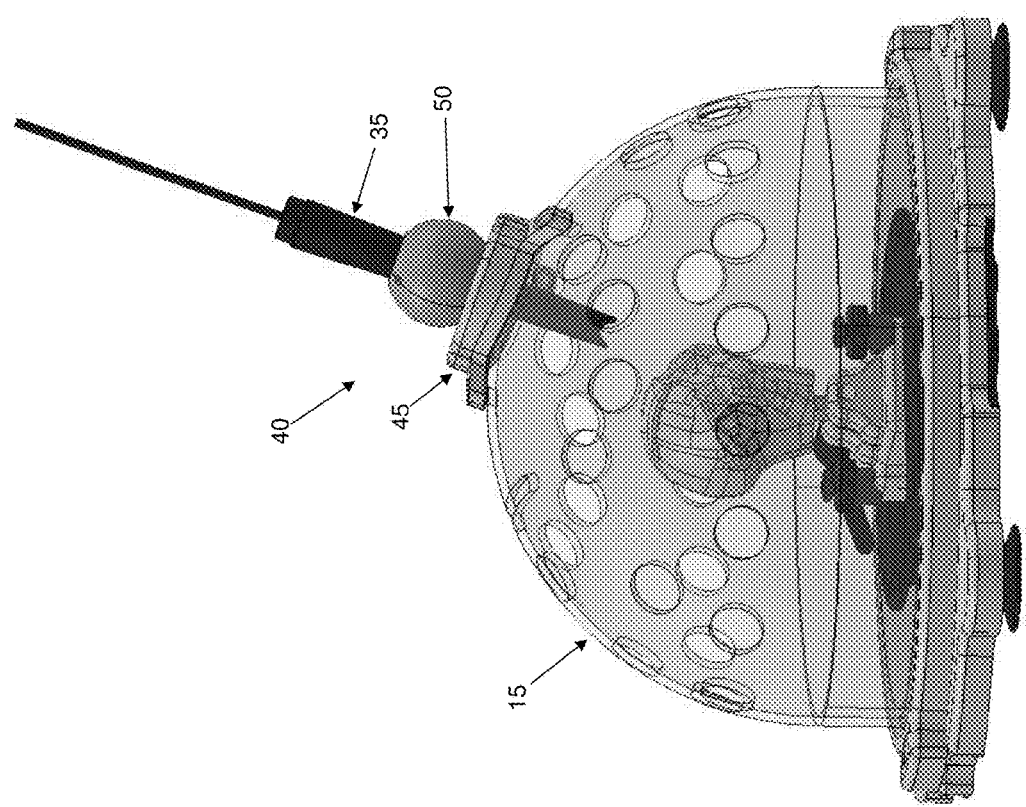
Figure 17:
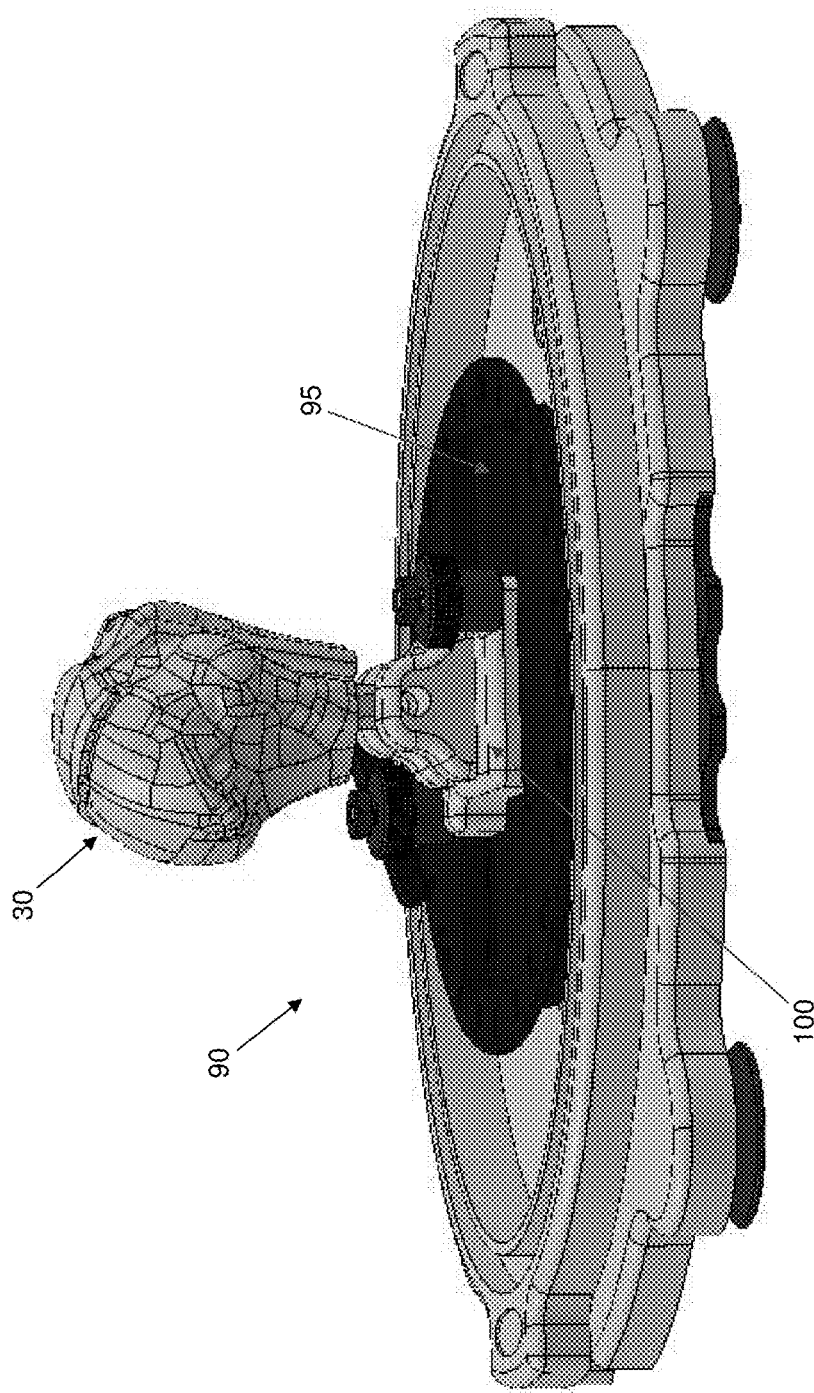
FIG. 17 is a schematic view showing a novel holder for mounting an anatomical model to an endoscopic training apparatus.
Figure 18:
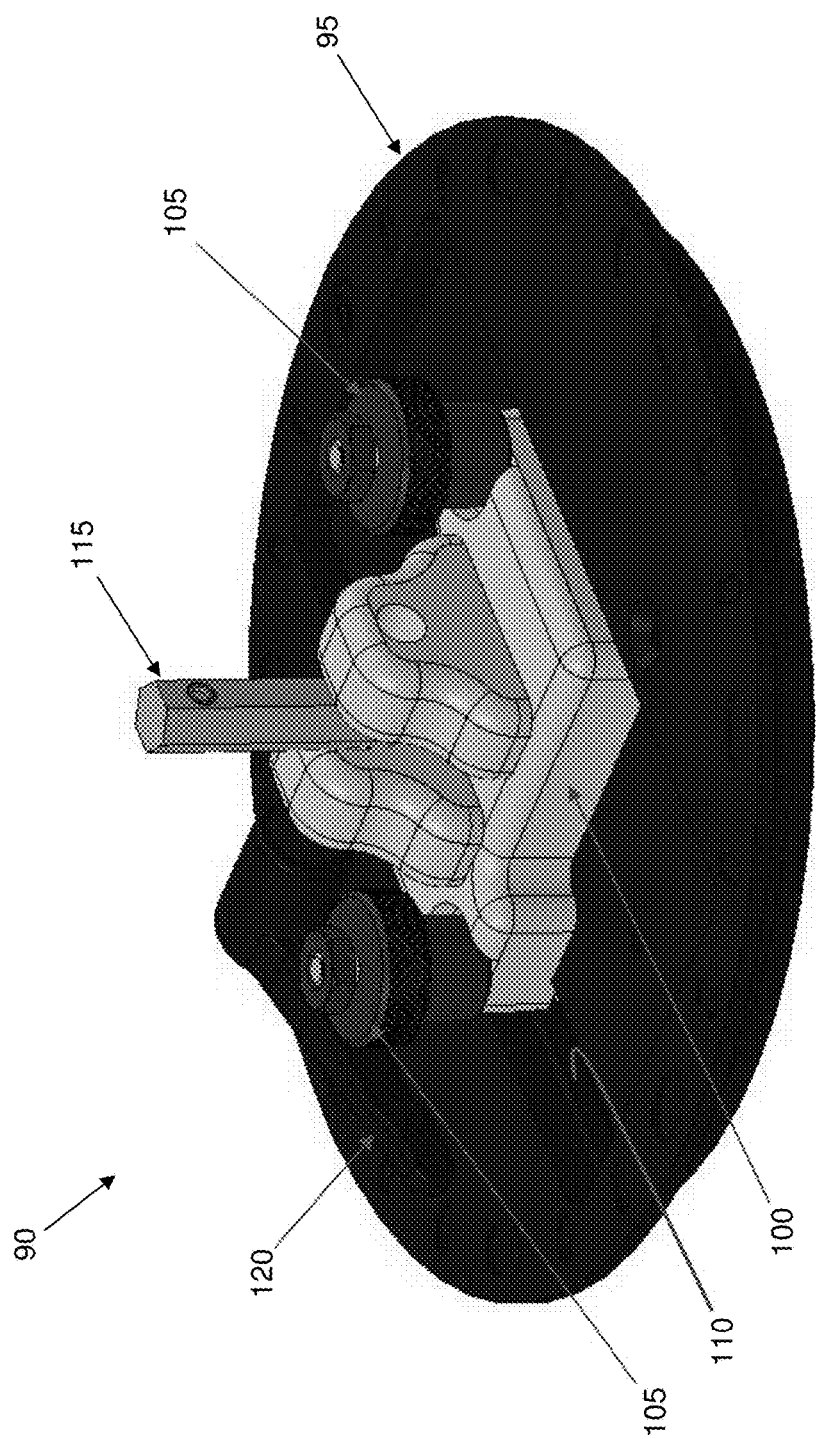
FIGS. 18-20 are schematic views showing further aspects of the novel holder shown in FIG. 17.
Figure 19:
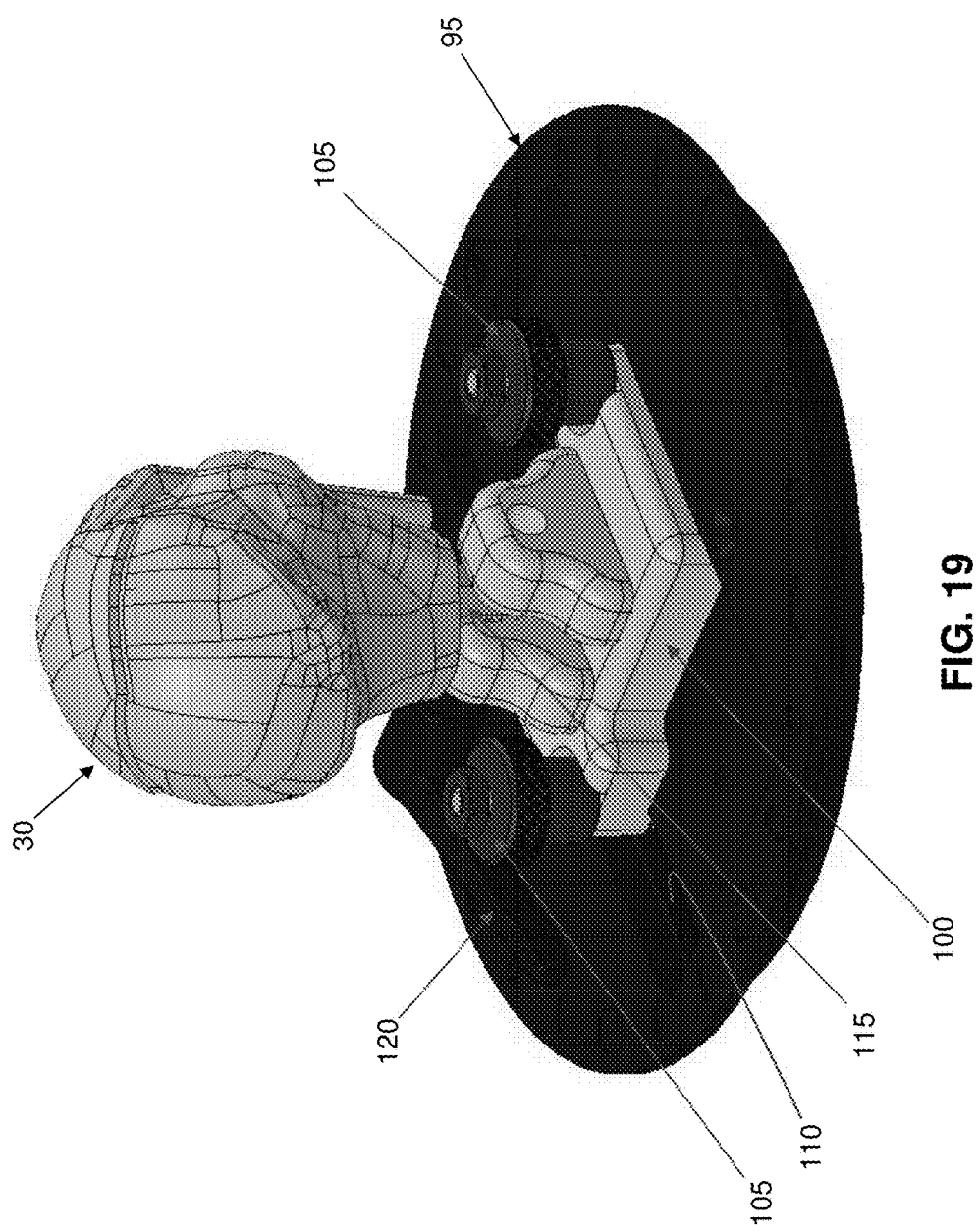

Looking next at FIGS. 8-10, base 45 generally comprises a central opening 55 (FIG. 8) which is configured to receive ball 50 (but which does not allow ball 50 to pass through central opening 55), and a plurality of legs 60 for releasably mounting base 45 to endoscopic training apparatus 5, as will hereinafter be discussed. More particularly, central opening 55 comprises a curvature about the perimeter of central opening 55 that is complementary to the curvature of ball 50, so that the periphery of central opening 55 can seat ball 50. Legs 60 may be curved away from base 45 (e.g., in the manner shown in FIG. 6) so that the bottom surface of base 45 matches the curvature of dome 15 of endoscopic training apparatus 5 (FIGS. 15 and 16). Each leg 60 comprises an opening 65 for receiving a fastener 67 (e.g., a screw) which is used to releasably secure mount 45 to dome 15 of endoscopic training apparatus 5 (see FIG. 15).

Base 45 preferably comprises a magnetized insert 70 (e.g., an insert formed out of a magnetic material such as a ferromagnet) which is disposed around central opening 55. Alternatively and/or additionally, base 45 may itself comprise a magnetized material, or base 45 may comprise a series of separate magnets disposed around central opening 55 of base 45.

As discussed above, central opening 55 is sized to be smaller than the diameter of ball 50, such that ball 50 cannot pass through central opening 55 (i.e., such that ball 50 sits "atop" base 45). In one preferred form of the present invention, magnetized insert 70 extends about the perimeter of central opening 55 of base 45 and generates a magnetic field at central opening 55 which is sufficient to retain ball 50 within (or "atop") central opening 55 of base 45. The magnetic field generated by insert 70 is strong enough to normally hold ball 50 (and a scope 35 passing through ball 50, as will hereinafter be discussed in further detail) fixed in position relative to base 45, however, the magnetic force is not so strong as to prevent the surgeon from manually pivoting ball 50 within central opening 55 of base 45 when the surgeon wishes to adjust the position of ball 50 (i.e., to adjust the position of a scope 35 mounted to ball 50) relative to the base 45, as will hereinafter be discussed in further detail.

Figure 10:
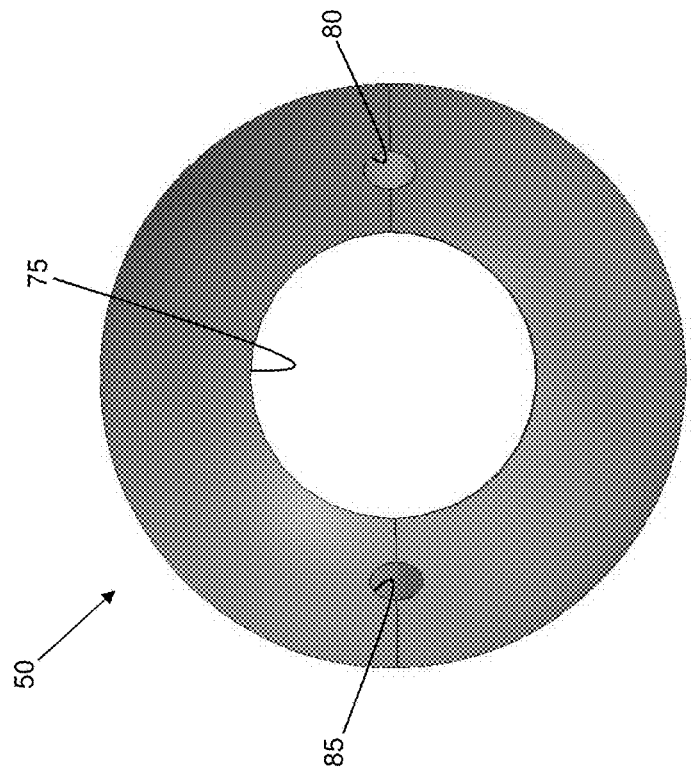
Figure 9:
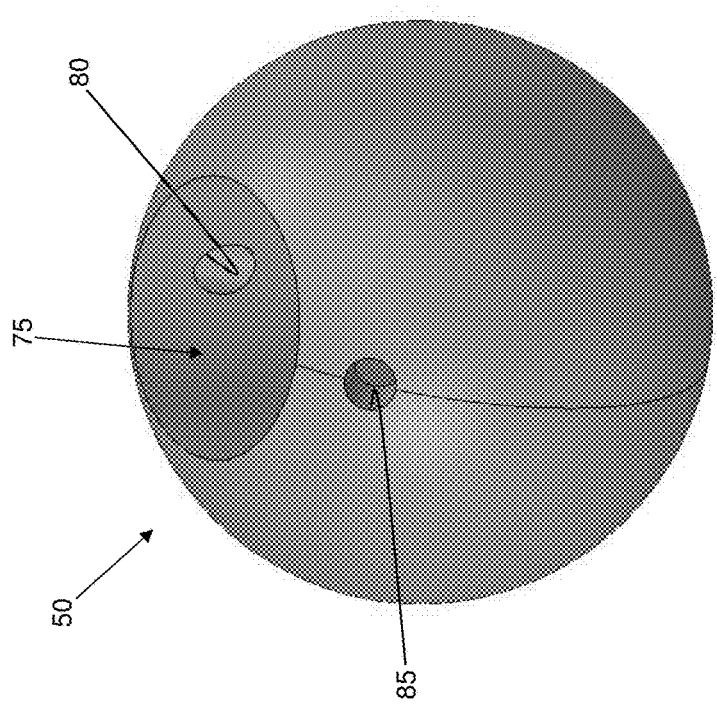
Figure 11:
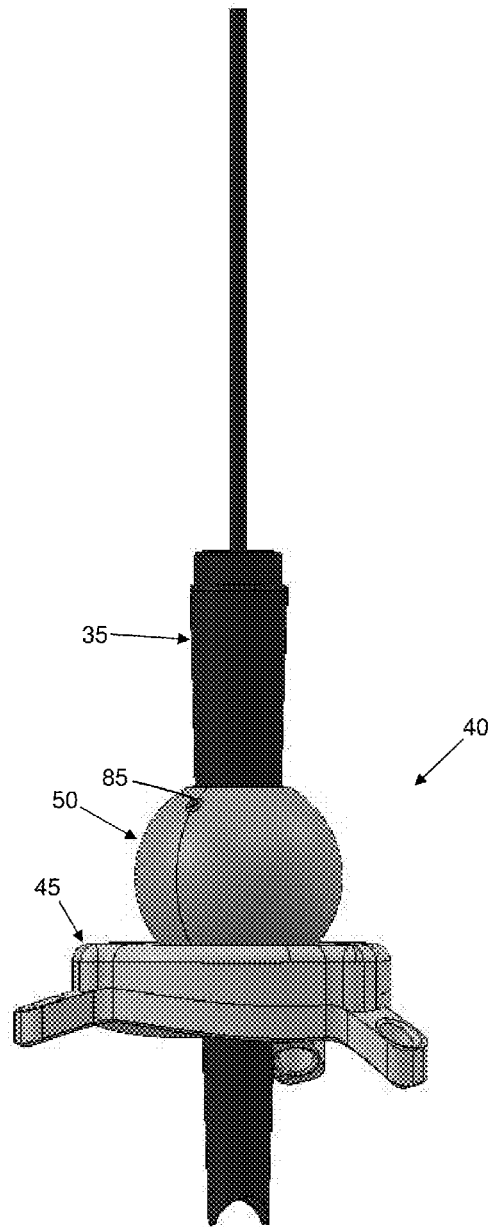
FIGS. 11-14 are schematic views showing further aspects of the novel mount of FIGS. 5-7, with a scope being disposed within the novel mount.
Figure 12:
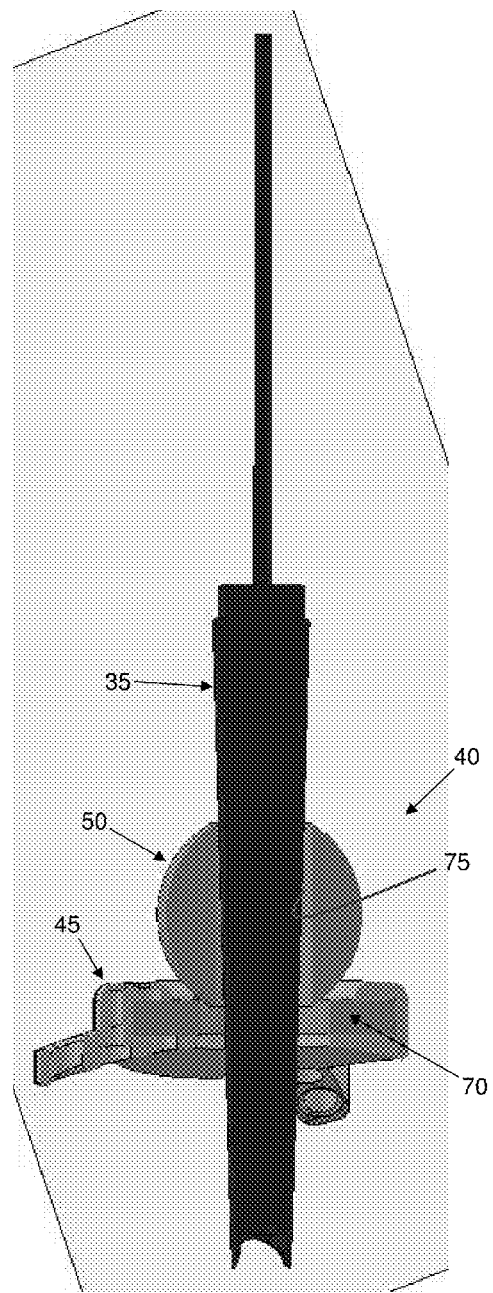
Figure 13:
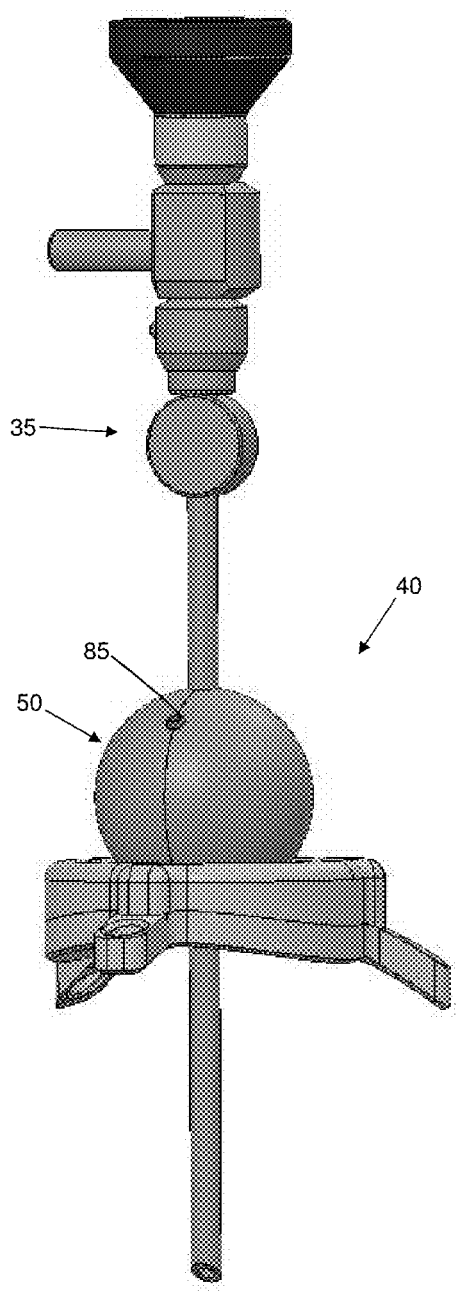
Figure 14:
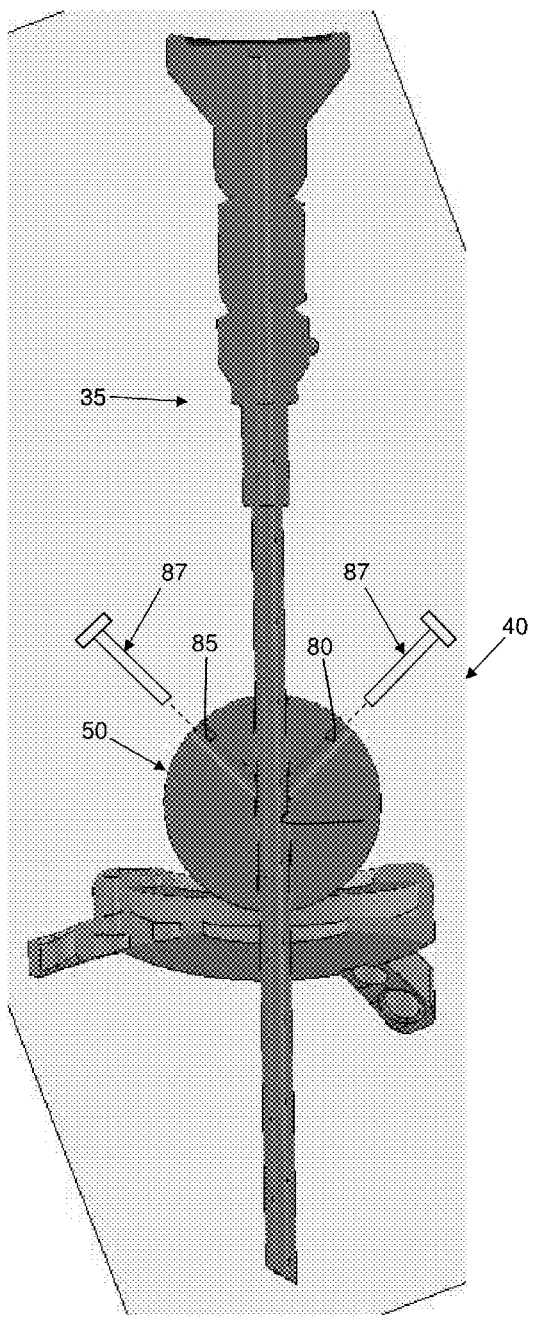

Looking next at FIGS. 9 and 10, ball 50 preferably comprises a steel structure of generally spherical shape having a central bore 75 passing therethrough. Central bore 75 is sized to slidably receive a scope 35 therein (FIGS. 11-14). It should be appreciated that central bore 75 can be dimensioned for accepting scopes of various diameters (i.e., one ball 50 may comprise a central bore 75 having a first diameter, and a second ball 50 may comprise a central bore 75 having a second, different diameter). See, for example, FIGS. 11 and 12 which show a ball 50 having a central bore 75 of a first diameter, and FIGS. 13 and 14 which show another ball 50 having a central bore 75 of a second, smaller diameter.

In one preferred form of the present invention, ball 50 also comprises two threaded cross-bores 80, 85 which intersect and open onto central bore 75. Cross-bores 80, 85 are preferably diametrically opposed from one another (FIGS. 10 and 14) so as to intersect central bore 75 from opposite sides of the central bore. In order to secure scope 35 in place within central bore 75, a set screw 87 (FIG. 14) can be advanced down one or both of cross-bores 80, 85 so as to engage the scope and retain it in position. Set screw(s) 87 act in a manner similar to the large screws that tighten against a Christmas tree in a Christmas tree stand, engaging the scope inserted into central bore 75 of ball 50, whereby to releasably lock the scope to ball 50. Set screw(s) 87 provide support to scope 35 inserted into central bore 75, allowing the depth of the insertion of the scope and the rotation of the scope to be adjusted and then secured by tightening set screw(s) 87 against the scope.

Use of the Novel Mount 40 with Endoscopic Training Apparatus 5

In use, and looking now at FIGS. 15 and 16, mount 40 is first aligned with a selected opening 20 formed on dome 15 of endoscopic training apparatus 5 such that central opening 55 of mount 40 is aligned with the selected opening 20. Next, mount 40 is mounted to endoscopic training apparatus 5 by passing one or more fasteners 67 through openings 65 of legs 60 of mount 40 into the exterior of dome 15, whereby to secure mount 40 in position against the outer surface of dome 15. Ball 50 is secured to base 45 of mount 40 by placing ball 50 into/onto central opening 55 of base 45 such that magnetized insert 70 holds ball 50 in place relative to base 45 and such that central bore 75 of ball 50 is aligned with central opening 55 of base 45.

A scope 35 (e.g., an endoscope, an arthroscope, etc.), is inserted into central bore 75 of ball 50 such that the scope passes through ball 50 and through opening 20 of dome 15. The surgeon adjusts the disposition of scope 35 such that the distal end of the scope is at the desired depth and such that the scope is rotated about its longitudinal axis to the desired position. One or more set screws 87 are then advanced into cross-bores 80, 85 formed in ball 50 and tightened against scope 35 so as to releasably lock the scope to ball 50.

Set screw(s) 87 can be loosened (i.e., retracted away from scope 35) when it is desired to change the depth and/or rotational disposition of the scope, and then re-tightened (i.e., advanced toward scope 35) when the scope has been properly positioned. More particularly, by loosening set screw(s) 87, scope 35 can be adjusted (e.g., moved up or down relative to ball 50, or rotated about the longitudinal axis of the scope relative to ball 50, etc.) as desired, and then locked in position by re-tightening set screw(s) 87.

Additionally, by manually pivoting ball 50 within the ring-shaped central opening 55 of base 45 of mount 40, the angular position of scope 35 relative to mount 40 (and hence relative to dome 15) can be adjusted as needed to address the surgical site. Due to the strength of the magnetic field provided by magnetized insert 70, ball 50 and scope 35 do not move unless manually manipulated by the surgeon (i.e., the strength of the magnetic field provided by magnetic insert 70 is sufficient to hold ball 50 and scope 35 stationary unless acted upon by a sufficiently-strong outside force).

It will be appreciated that, once the camera is in the appropriate position and stable, the surgeon can practice an endoscopic surgical procedure without the need for an assistant to hold or adjust scope 35, since the scope is maintained in position by the interaction of ball 50 and magnetic insert 70. If it is desired to vary the depth of scope 35 within the cavity (i.e., the volume enclosed by dome 15), or the rotational disposition of scope 35 relative to ball 50, the surgeon loosens the one or more set screw(s) 87 disposed in threaded cross-bore(s) 80, 85, repositions the scope as desired, and then re-tightens set screw(s) 87 so as to stabilize the scope and maintain the scope in position. Furthermore, if it is desired to vary the angular disposition of scope 35 relative to mount 40 (and hence, relative to dome 15), the surgeon pivots ball 50 within central opening 55 of base 45 of mount 40 as desired. The surgeon can then practice an endoscopic surgical procedure (e.g., suture anchor positioning, stitching, knot tying, etc.) using endoscopic training apparatus 5 without requiring an assistant to hold scope 35 in position.

Although mount 40 has been discussed in the context of a mount for attachment to endoscopic training apparatus 5, it should be appreciated that mount 40 can be used for many other applications and is not intended to be limited to use with an endoscopic training apparatus. By way of example but not limitation, mount 40 may serve as a support (and aiming) device for a standard camera, a tubular camera, or any type of camera or other device that needs to be held in place while simultaneously preserving the ability to change directions and depth while maintaining support.

Additional Features of the Invention

As discussed above, mount 40 provides a fast and effective way for a surgeon to releasably and adjustably mount a scope 35 to an endoscopic training apparatus 5.

However, it has also been recognized that it may be desirable to quickly and easily mount a model of the anatomy to be practiced on (e.g., model 30) to baseplate 10 of endoscopic training apparatus 5 in such a way that the position of the model can be adjusted. To that end, and looking now at FIGS. 17-20, there is shown a novel holder 90 formed in accordance with the present invention.

Figure 20:
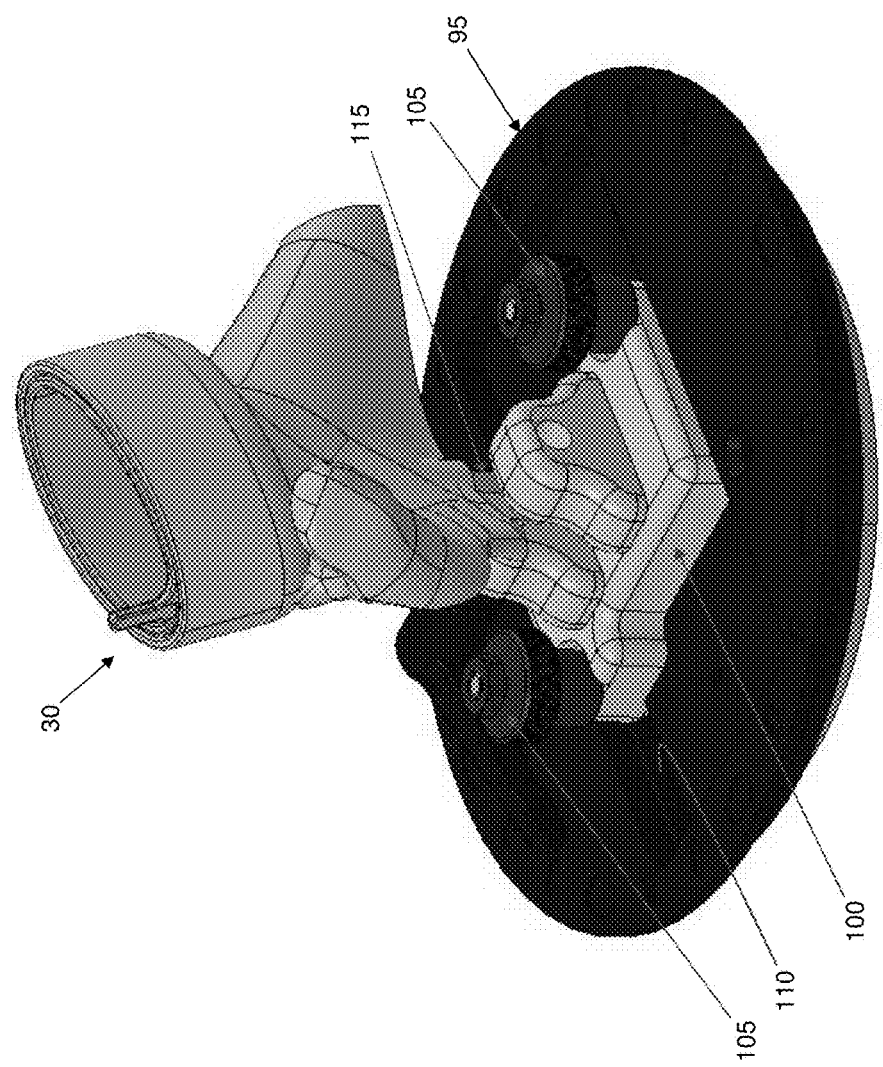

Holder 90 generally comprises a base 95 and a body 100 slidably mounted to base 95. More particularly, body 100 is slidably attached to base 95 via a pair of set screws 105 which pass through body 100 and are received in slots 110 formed in base 95. A post 115 is pivotally mounted to body 100 via a shaft (not shown) which is connected to a lever 120. Rotation of lever 120 causes post 115 to pivot relative to body 100. A model of the anatomy to be practiced on (e.g., model 30) may be mounted to post 115 of body 100 of base 95, and base 95 may be mounted to baseplate 10 of endoscopic training apparatus 5 (e.g., via one or more set screws, via magnetic mounting, etc.). The lateral and angular disposition of the anatomical model (e.g., model 30) may then be adjusted by (i) adjusting the lateral disposition of body 100 of holder 90 relative to base 95 (i.e., by loosening set screws 105, moving body 100 laterally along slots 110 and then re-tightening set screws 105) and/or (ii) adjusting the angular disposition of post 115 by rotating lever 120 until the anatomical model is disposed at the desired angle. By way of example but not limitation, model 30 may comprise a portion of the humerus (FIG. 19) or model 30 may comprise a portion of the scapula (FIG. 20).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for releasably and adjustably mounting a tubular device to an object, said apparatus comprising:
   a base comprising a central opening passing therethrough, said base being magnetized so as to provide a magnetic field at said central opening of said base;
   a generally spherical ball sized to be received in said central opening of said base but sized so as to not pass through said central opening, said generally spherical ball comprising a central bore passing therethrough;
   wherein said ball comprises a ferrous material which is attracted to the magnetic field at said central opening of said base, and further wherein said magnetic field at said central opening of said base is sufficiently strong so as to retain said ball in said central opening of said base; and wherein said central bore of said generally spherical ball is configured to slidably receive a tubular device therein, and further wherein said base is configured to be mounted to an object.

2. Apparatus according to claim 1 wherein said base further comprises at least one magnetic insert for providing said magnetic field.

3. Apparatus according to claim 2 wherein said at least one magnetic insert is disposed about a perimeter of said central opening of said base.

4. Apparatus according to claim 1 wherein said central bore of said generally spherical ball is sized to receive a surgical scope.

5. Apparatus according to claim 1 wherein said tubular device is one selected from the group consisting of an endoscope and an arthroscope.

6. Apparatus according to claim 1 wherein said generally spherical ball further comprises at least one cross-bore which intersects said central bore of said generally spherical ball.

7. Apparatus according to claim 6 wherein said at least one cross-bore is threaded.

8. Apparatus according to claim 7 wherein said at least one cross-bore receives at least one set screw therein.

9. Apparatus according to claim 6 wherein said generally spherical ball comprises two cross-bores, and further wherein said two cross-bores are diametrically opposed from one another.

10. A method for releasably and adjustably mounting a scope to an endoscopic training apparatus, said method comprising:
    providing apparatus comprising:
        a base comprising a central opening passing therethrough, said base being magnetized so as to provide a magnetic field at said central opening of said base;
        a generally spherical ball sized to be received in said central opening of said base but sized so as to not pass through said central opening, said generally spherical ball comprising a central bore passing therethrough;
    wherein said ball comprises a ferrous material which is attracted to the magnetic field at said central opening of said base, and further wherein said magnetic field at said central opening of said base is sufficiently strong so as to retain said ball in said central opening of said base; and
    wherein said central bore of said generally spherical ball is configured to slidably receive a scope therein, and further wherein said base is configured to be mounted to an endoscopic training apparatus;
    mounting said base to an endoscopic training apparatus such that said central opening of said base and said central bore of said generally spherical ball are aligned with an opening in the endoscopic training apparatus; and
    disposing a scope in said central bore of said generally spherical ball such that the scope is releasably and adjustably retained in said central bore of said generally spherical ball.

11. A method according to claim 10 wherein said base further comprises at least one magnetic insert for providing said magnetic field.

12. A method according to claim 11 wherein said at least one magnetic insert is disposed about a perimeter of said central opening of said base.

13. A method according to claim 10 wherein said scope is one selected from the group consisting of an endoscope and an arthroscope.

14. A method according to claim 10 wherein said generally spherical ball further comprises at least one cross-bore which intersects said central bore of said generally spherical ball.

15. A method according to claim 14 wherein said at least one cross-bore is threaded.

16. A method according to claim 15 wherein said at least one cross-bore receives at least one set screw therein.

17. A method according to claim 14 wherein said generally spherical ball comprises two cross-bores, and further wherein said two cross-bores are diametrically opposed from one another.

18. Apparatus for releasably and adjustably mounting an anatomical model to an object, said apparatus comprising:
    a base;
    a body slidably mounted to said base by a pair of diametrically-opposed set screws; and
    a post pivotally mounted to the base, said post being configured to be selectively pivoted by rotation of a lever.

* * * * *